DitUnited States Patent [19]

Kukolja et al.

[11] 4,335,240
[45] Jun. 15, 1982

[54] PROCESS FOR CYCLIZATION

[75] Inventors: Stjepan Kukolja, Carmel; Janice L. Pfeil, Indianapolis, both of Ind.

[73] Assignee: Eli Lilly and Company, Indianapolis, Ind.

[21] Appl. No.: 264,263

[22] Filed: May 18, 1981

Related U.S. Application Data

[62] Division of Ser. No. 137,862, Apr. 7, 1980, Pat. No. 4,293,493.

[51] Int. Cl.$^3$ .......................................... C07D 498/02
[52] U.S. Cl. ..................................................... 544/90
[58] Field of Search ........................................... 544/90

[56] References Cited

U.S. PATENT DOCUMENTS

| | | | |
|---|---|---|---|
| 3,872,086 | 3/1975 | Barton et al. | 260/239 A |
| 3,954,732 | 5/1976 | Kamiya et al. | 424/271 |
| 4,024,152 | 5/1977 | Kukolja | 260/239 A |
| 4,066,641 | 1/1978 | Hamashima et al. | 260/239 A |
| 4,071,513 | 1/1978 | Kim | 260/239 A |

OTHER PUBLICATIONS

Barton et al., Chem. Comm., (1971), p. 1137.
Kamiya et al., Tet Letters (1973), p. 3001.
Kim et al., Tet Letters (1978), p. 409.
Masamure et al., J. Amer. Chem. Soc., vol. 97 (1975), p. 3515.
Wolfe et al., Can. J. Chem., vol. 52 (1974), p. 3996.
Naylor et al., The Chemical Society, London, 1977, pp. 204-213.
Narisada et al., Heterocyclics, vol. 7 (1977), pp. 839-849.

*Primary Examiner*—Richard Raymond
*Attorney, Agent, or Firm*—William B. Scanlon; Arthur R. Whale

[57] ABSTRACT

Azetidinone alcohol disulfides are synthesized by reduction of the corresponding aldehydes. The azetidinone alcohol disulfides are the substrates for a process which cyclizes these compounds to 1-oxa $\beta$-lactam compounds, employing a cyclizing reagent chosen from the class consisting of divalent mercury salts or trivalent phosphine compounds. The 1-oxa $\beta$-lactam compounds produced by this process are intermediates in the synthesis of 1-oxa $\beta$-lactam antibiotics.

26 Claims, No Drawings

PROCESS FOR CYCLIZATION

This application is a division of application Ser. No. 137,862, filed Apr. 7, 1980, now U.S. Pat. No. 4,293,493.

BACKGROUND OF THE INVENTION 1-oxa β-lactam compounds, which possess the following general structure:

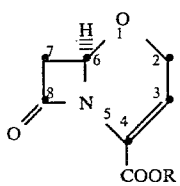

have recently been the subject of extensive research efforts due to their antibacterial activity. Specifically, there have been some recent reports of syntheses of 1-oxa β-lactam compounds substituted with methyl at the C-3 position. For example, Naylor et al. in "Recent Advances in the Chemistry of β-Lactam Antibiotics" (J. Elks, ed.), The Chemical Society, London, 1977, p. 204, reported a synthesis of 1-oxacephalexin. Similarly, Narisada et al., *Heterocycles*, 7, 839 (1977), were able to prepare several 3-methyl 1-oxa β-lactam compounds which exhibited antibacterial activity from four to eight times greater than the corresponding cephalosporins. The free acids of 7β-acylamino-7α-alkoxy-3-methyl 1-oxa β-lactam compounds, and the antibacterial activity thereof, are disclosed by Merck and Company in South African patent application No. 738503, filed May 11, 1973. The present application describes and claims novel intermediates which can be employed in the synthesis of the aforementioned biologically active 7β-acylamino-7α-alkoxy-3-methyl 1-oxa β-lactam compounds. The process for the conversion of such intermediates into other unclaimed intermediates in the synthesis of the aforementioned 1-oxa β-lactam antibiotics is an alternate aspect of this invention.

SUMMARY OF THE INVENTION

This invention is directed to azetidinone alcohol disulfide compounds, encompassing both unsymmetrical azetidinone alcohol disulfide compounds, specifically the aryl 4R[1-(protected carboxy 2N-3-methyl-4-ol-Z-but-2-ene-oate)-2-oxo-3S-acylamino azetidine] disulfide compounds, and symmetrical azetidinone alcohol disulfide compounds, specifically the 4R, 4'R-bis[1-(protected carboxy 2-N-3-methyl-4-ol-Z-but-2-ene-oate)-2-oxo-3S-acylamino azetidine] disulfide compounds, and the process for cyclizing these compounds to the corresponding 7α-acylamino-3-methyl 1-oxa β-lactam compounds. The azetidinone alcohol disulfide compounds of this invention are synthesized by the sodium cyanoborohydride reduction of the corresponding aldehydes. The azetidinone alcohol disulfide compounds are then used as the substrates in the process of this invention, which involves cyclizing the disulfide compounds to the corresponding 7α-acylamino-3-methyl 1-oxa β-lactam compounds. The cyclizing reagents used in the process are chosen from a class consisting of either (a) alkyl, aryl or mixed alkyl-aryl phosphines, or (b) dichloromercury (II), dibromomercury (II), or bis(trifluoroacetato)mercury (II).

The 7α-acylamino-3-methyl 1-oxa β-lactam compounds produced by the process of this invention are intermediates in the synthesis of the general class of antibiotically active 7β-acylamino-7α-methoxy-3-methyl 1-oxa β-lactam compounds.

DETAILED DESCRIPTION OF THE INVENTION

This invention is directed to compounds of the following general formula I,

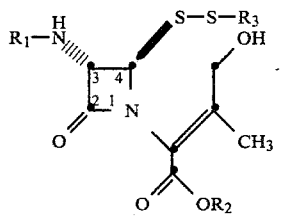

and the process for their conversion to a 1-oxa β-lactam compound. These compounds are referred to in this application, for convenience sake, as either "symmetrical azetidinone alcohol disulfide" or "unsymmetrical azetidinone alcohol disulfide" compounds, depending on the moieties bonded to the disulfide group. In the above terms, "symmetrical" refers to the presence of identically substituted azetidinone moieties bonded to either end of the disulfide group, while "unsymmetrical" refers to presence of an azetidinone moiety and an aromatic ring moiety bonded to each end disulfide group. The word "alcohol" in the above terms calls attention to the fact that the requisite group is present for cyclization of the disulfide compounds, as opposed to the aldehyde group which must be reduced to the alcohol before cyclization can occur.

The 1-oxa β-lactam antibiotics obtained from the azetidinone disulfides of the invention possess the following bicyclic ring system:

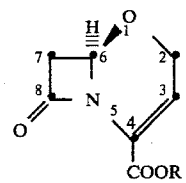

wherein R can be hydrogen or a conventional carboxylic acid protecting group.

In the formulas contained in this application, the mark " ▬ " means β-configuration and the dotted line " ╌ " means α-configuration.

The azetidinone alcohol disulfide compounds of this invention are represented by the following general formula I

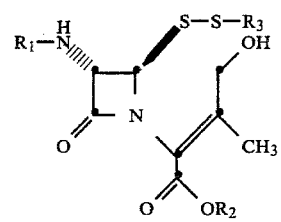

wherein R₁ is an acyl group of the formula

wherein R' is (a) $C_1$-$C_7$ alkyl, cyanomethyl, $C_1$-$C_6$ haloalkyl, 4-protected amino-4-protected carboxybutyl; or (b) $C_1$-$C_6$ alkoxy, phenoxy, benzyloxy or 4-methoxybenzyloxy; or (c) the group —R" wherein R" is phenyl or substituted phenyl wherein the substituents are 1 or 2 halogens, protected hydroxy, cyano, trifluoromethyl, $C_1$-$C_4$ alkyl, $C_1$-$C_4$ alkoxy, protected carboxy, protected carboxymethyl, protected hydroxymethyl or protected aminomethyl; or (d) an arylalkyl group of the formula R"—(O)$_m$—CH₂— wherein R" is as defined above, and m is 0 or 1; or (e) a substituted arylalkyl group of the formula

wherein R'" is R" as defined above, 2-thienyl, 3-thienyl, 2-furyl or 3-furyl; W is protected hydroxy, protected carboxy, protected amino, or (f) a heteroarylmethyl group of the formula R""—CH₂— wherein R"" is 2-thienyl, 3-thienyl, 2-furyl, 3-furyl, 2-thiazolyl, 5-tetrazolyl, or 1-tetrazolyl;

R₂ is a conventional carboxy protecting group and R₃ is another molecule of the identically substituted azetidinone alcohol moiety bonded to the opposite end of the disulfide group, or is phenyl or a mono-substituted phenyl group, where the substituents are chloro, methoxy, methyl or acetoxy.

In the following specification, the protecting group designation is omitted for simplicity in nomenclature, but it is understood that, in the description of the process of this invention, each carboxy, hydroxy or amino group is a protected group.

In the foregoing definitions of the compounds of this invention, the term "$C_1$-$C_7$ alkyl" refers to methyl, ethyl, n-propyl, n-butyl, isobutyl, pentyl, n-hexyl, cyclohexyl, n-heptyl and like aliphatic hydrocarbon groups.

The term "$C_1$-$C_6$ haloalkyl" refers to chloromethyl, bromomethyl, iodomethyl, 2-bromoethyl, 2-chloroethyl, 2-bromopropyl, 2-iodopropyl, 2-chlorobutyl, 2-bromo-2-methylpropyl, 2-bromobutyl, 2-bromo-2-methylbutyl and like groups.

The term, "protected amino" as employed in the above definition has reference to an amino group substituted with one of the commonly employed amino blocking groups such as the tert-butoxycarbonyl group (t-BOC) the benzyloxycarbonyl group, the 4-methoxybenzyloxycarbonyl group, the 2,2,2-trichloroethoxycarbonyl group, the trimethylsilyl group, and like amino protecting groups. The nature of such amino protecting groups is not critical so long as the protected amino functionality is stable under the reaction conditions described hereinafter.

The term "protected hydroxy" has reference to any group stable under the reaction conditions of the subsequent step in this synthesis of the 1-oxa β-lactam compounds, but readily cleavable thereafter. Such groups include the formyloxy group, the chloroacetoxy group, the benzhydryloxy group, the trityloxy group, the trimethylsilyl group, and the like.

The term "protected carboxy" has reference to a carboxy group which has been esterified with one of the commonly used carboxylic acid protecting ester groups employed to block or protect the carboxylic acid functionality while reactions involving other functional sites of the compound are carried out. Such protected carboxy groups are noted for their ease of cleavage by hydrolytic methods to the corresponding carboxylic acid. Examples of carboxylic acid protecting groups include tert-butyl, p-methoxybenzyl, diphenylmethyl, 2,4,6-trimethylbenzyl, trityl, 4-methoxytrityl, 4,4'-dimethoxytrityl, 4,4',4"-trimethoxytrityl and like ester forming moieties. The nature of such ester forming groups is not critical so long as the ester formed therewith is stable under the reaction conditions described hereinafter. Preferred carboxylic acid protecting groups are diphenylmethyl, 4-methoxybenzyl, and tert-butyl.

In the foregoing definitions, hydroxy, amino, and carboxy protecting groups are not exhaustively defined. The function of such groups is to protect the reactive functional groups during the preparation of the desired products and then be removed without disrupting the remainder of the molecule. Many such protecting groups are well known in the art and the use of other groups equally applicable to the process and compounds of the present invention, such as those described in J. F. W. McOmie, "Protective Groups in Organic Chemistry", Plenum Press, 1973, will be recognized as suitable. Thus, there is no novelty or inventiveness asserted with regard to the "protecting groups" alluded to in this specification.

When in the above definition R" represents a substituted phenyl group, R" can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or dihydroxyphenyl group such as 4-hydroxyphenyl, 3-hydroxyphenyl, 2,4-dihydroxyphenyl and the like; a cyanophenyl group, for example, 4-cyanophenyl; a mono or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono or disubstituted lower alkylphenyl ether for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, R" represents disubstituted phenyl groups wherein the substituents can be different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and like disubstituted phenyl groups bearing different substituents.

Illustrative of the acyl groups,

where R' is $C_1$-$C_7$ alkyl, or $C_1$-$C_6$ haloalkyl are acetyl, propionyl, butyryl, hexanoyl, chloroacetyl, bromoacetyl and the like.

Representative of the acyl groups

when R' is phenyl or substituted phenyl are benzoyl, 2,6-dimethoxybenzoyl, 4-chlorobenzoyl, 4-methylbenzoyl, 3,4-dichlorobenzoyl, 4-cyanobenzoyl, 3-bromobenzoyl, and 3-aminobenzoyl and like substituted phenylacetyl groups.

Illustrative of the acyl groups

when R' is a group of the formula R"—(O)$_m$—CH$_2$—, m is O and R" is phenyl or substituted phenyl, are phenylacetyl, 4-chlorophenylacetyl, 3-hydroxyphenylacetyl, 3-cyanophenylacetyl, 4-hydroxy-3-methylphenylacetyl, 4-bromophenylacetyl, 4-ethoxyphenylacetyl, 3,4-dimethoxyphenylacetyl and the like; and when m is 1, representative groups are phenoxyacetyl, 3-hydroxyphenoxyacetyl, 4-chlorophenoxyacetyl, 3,4-dichlorophenoxyacetyl, 2-chlorophenoxyacetyl, 4-methoxyphenoxyacetyl, 2-ethoxyphenylacetyl, 3,4-dimethylphenoxyacetyl, 4-isopropylphenoxyacetyl, 3-cyanophenoxyacetyl and like substituted phenoxyacetyl groups.

Illustrative of the acyl groups when R' is a substituted aryl group of the formula

are the carboxy substituted acyl groups such as the 2-carboxy-2-phenylacetyl group of the formula

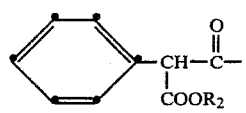

and similar groups wherein the phenyl ring is substituted, for example, 2-carboxy-2-(4-chlorophenyl)acetyl, 2-carboxy-2-(4-methoxyphenyl)acetyl, 2-carboxy-2-(2-thienyl)acetyl, 2-carboxy-2-(4-methylphenyl)acetyl, 2-carboxy-2-(4-carboxymethyl)phenyl)acetyl, 2-carboxy-2-(4-hydroxymethylphenyl)acetyl and like groups.

Representative of the acyl groups when R' is a hydroxy substituted arylalkyl group are 2-hydroxy-2-(4-methoxyphenyl)acetyl, 2-hydroxy-2-(3-chloro-4-hydroxyphenyl)acetyl, 2-hydroxy-2-(3-bromophenyl)acetyl, 2-hydroxy-2-(3,5-dichloro-4-hydroxyphenyl)acetyl, 2-hydroxy-2-(3-chloro-4-methoxyphenyl)acetyl, 2-hydroxy-2-(3-chlorophenyl)acetyl, 2-hydroxy-2-(4-aminomethylphenyl)acetyl, 2-hydroxy-2-(3-thienyl)acetyl.

When R' is an amino substituted arylalkyl group, acyl groups represented thereby include 2-amino-2-phenylacetyl, 2-amino-2-(4-cyanophenyl)acetyl, 2-amino-2-(4-hydroxyphenyl)acetyl, and like groups.

Representative of the acyl group

when R' is a heteroarylmethyl group of the formula R""'—CH$_2$— are 2-thienylacetyl, 3-thienylacetyl, 2-furylacetyl, 2-thiazolylacetyl, 1-tetrazolylacetyl, a 5-tetrazolylacetyl and the like.

When in the above definition R$_3$ is a monosubstituted phenyl group where the substituents are chloro, methoxy, methyl or acetoxy, the substituent can be in the ortho, meta or para position. Such substituted R$_3$ groups include 4-chlorophenyl, 2-chlorophenyl, 4-methoxyphenyl, 3-methoxyphenyl, 4-methylphenyl, 2-methylphenyl, 4-acetoxyphenyl, 3-acetoxyphenyl and the like.

The compounds of this invention are synthesized by reducing the corresponding azetidinone aldehyde disulfide with sodium cyanoborohydride in an acidic medium at ambient temperatures. In general, the substrate azetidinone aldehyde disulfide is dissolved in wet tetrahydrofuran (THF), the resulting solution's pH is adjusted to about 3.5, and approximately 1 mole of sodium cyanoborohydride per mole of each aldehyde group present is added to the solution. As the reduction occurs the pH of the reaction solution is maintained between about 3.2 and about 3.6. After an appropriate time (e.g., about 0.5 hour to about 2 hours), the reaction solution is poured into a mixture composed of saturated sodium chloride solution and ethyl acetate. The desired azetidinone alcohol disulfide can be subsequently isolated from the ethyl acetate layer.

The above procedure used to synthesize azetidinone alcohol disulfides by reducing the corresponding azetidinone aldehyde disulfide was adopted from the procedures set forth in R. F. Borch, M. D. Bernstein, and H. D. Durst, *Journal of the American Chemical Society*, 93 2897 (1971).

The process of this invention for preparing the 7α-acylamino-3-methyl 1-oxa β-lactam compounds comprises reacting the azetidinone disulfide alcohol compounds of this invention with a cyclization reagent selected from among the group consisting of divalent mercury compound or a trivalent phosphorus compound in an inert organic solvent to give the desired 1-oxa β-lactam compound. The process of this invention is illustrated by the following general reaction scheme:

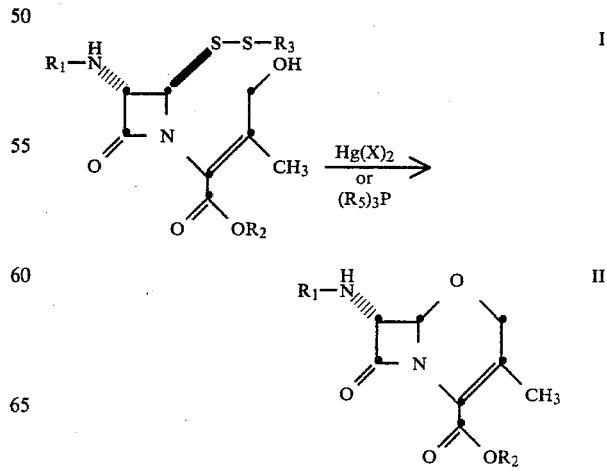

In the above general formula, $R_1$, $R_2$ and $R_3$ are as described before, X is chloro, bromo or trifluoroacetato and each $R_5$ is independently $C_1$ to $C_7$ alkyl, phenyl or phenyl substituted with $C_1$ to $C_4$ alkyl or $C_1$ to $C_4$ alkoxy.

The process of this invention is carried out by reacting an azetidinone disulfide alcohol with at least about 1 mole of the cyclization reagent per mole of the disulfide in an inert organic solvent in an inert atmosphere.

The process can be carried out at ambient temperatures, however, with the divalent mercury reagent cyclization proceeds at somewhat lower or higher temperatures as well, for example, between about 0° C. and about 45° C. When in the process of phosphine, $(R_5)_3P$, is used as the cyclizing agent the process proceeds best at somewhat elevated temperatures, for example, between about 40° C. to about 65° C. The process employing the phosphine cyclizing reagent can, however, be carried out over a broader temperature range of about 0° C. to about 100° C.

Although at least about 1 molar equivalent of either the mercury or phosphorus cyclization reagent is required for complete conversion, it is preferable to employ between about 4 and about 5 moles of the mercury cyclization reagent or between about 1.5 and about 2.5 moles of the phosphorus cyclization reagent per mole of the disulfide substrate.

Inert solvents employed in the process are those which are unreactive with the cyclizing reagent, the azetidinone disulfide and the cyclization product. Solvents used in the process when a divalent mercury reagent is the cyclizing agent are preferably somewhat polar organic solvents, (e.g. acetonitrile) owing to the enhanced solubility of the mercury reagents in these solvents. The process can also proceed with a divalent mercury reagent in less polar solvents, for example, methylene chloride.

Examples of inert organic solvents that can be employed when the trivalent phosphine reagent is used include methylene chloride, 1,2-dichloroethane, chlorobenzene, 1,1-dibromo-2-chloroethane, benzene, toluene, xylenes, cyclohexane, cyclopentane, 2-methylbutane, 2,2,4-trimethylpentane, hexane, heptane, acetonitrile, benzonitrile, pyridine, piperidine, pyrrolidine, and the like. 1,2-Dichloroethane is the preferred solvent for the process where the trivalent phosphorus cyclization reagent is employed. However, chloroform and carbon tetrachloride cannot be used as solvents when the trivalent phosphine reagents is used as the cyclizing agent due to their reactivity toward phosphines.

Examples of solvents which can be used with the divalent mercury reagent include the organonitriles, for example, acetonitrile, propionitrile and butyronitrile, ether solvents, for example, tetrahydrofuran, dioxane, the dimethyl ether of ethylene glycol, diethylether and dibutyl ether; ketones, for example, acetone, methylethyl ketone and diethyl ketone; esters, for example, ethyl acetate, methyl acetate, isoamyl acetate, methyl butyrate and ethyl propionate; and amides such as N,N-dimethylformamide, N,N-dimethylacetate or hexamethylphosphoric triamide (HMPA). Nitrile solvents are preferred when the divalent mercury reagent is used as the cyclization agent.

As mentioned above, in the general formula for the trivalent phosphorus cyclization reagent, $R_5$ can be $C_1$ to $C_7$ alkyl, phenyl, or phenyl substituted with $C_1$ to $C_4$ alkyl or $C_1$ to $C_4$ alkoxy. The terms "$C_1$ to $C_7$ alkyl" is as described above. The term "$C_1$ to $C_4$ alkyl" includes methyl, ethyl, isopropyl, n-propyl, n-butyl, sec-butyl, tert-butyl and iso-butyl. Representative "$C_1$ to $C_4$ alkoxy" groups are methoxy, ethoxy, isopropoxy, tert-butoxy and n-butoxy.

Illustrative of the trivalent phosphorus cyclization reagents which can be employed are alkyl phosphines such as trimethylphosphine, triethylphosphine, tripropylphosphine, tri(iso-propyl)phosphine, tributylphosphine, tri(tert-butyl)phosphine, tricyclohexylphosphine, tri(4-methylcyclohexyl)phosphine and the like; aryl phosphines such as triphenylphosphine, tri(p-tolyl)phosphine, tri(o-tolyl)phosphine, tri(m-tolyl)phosphine, tri(p-n-propylphenyl)phosphine, tri(p-tert-butylphenyl)phosphine, tri(p-methoxyphenyl)phosphine, tri(p-isopropoxyphenyl)phosphine, o-methoxyphenyldiphenylphosphine, p-methoxyphenyldiphenyl phosphine, and the like; and phosphines containing both alkyl and aryl groups, such as dimethylphenylphosphine, diphenylethylphosphine, di(p-methoxyphenyl)methylphosphine, di(p-tolyl)methylphosphine, p-methoxyphenylphenylmethylphosphine, p-tolylphenylmethylphosphine and the like. The preferred phosphine for use in the process is triphenylphosphine.

As mentioned above, when the process of this application is carried out with the divalent mercury cyclization reagent, the general formula of this reagent is $$Hg(X)_2$$

wherein X is chloro, bromo or trifluoroacetato. The divalent mercury cyclization reagents which can be employed in the present process are dichloromercury(II), dibromomercury(II) or bis(trifluoroacetato)mercury(II). The preferred divalent mercury cyclization reagent is bis(trifluoroacetato)mercury(II).

A preferred group of azetidinone alcohol disulfide compounds described by this invention which can be converted to the 7α-acylamino-3-methyl 1-oxa β-lactam compounds according to the process of this invention are represented by the following general formula

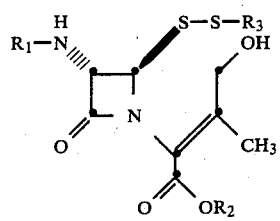

wherein $R_1$ is an acyl group of the formula

wherein R' is
(a) $C_1$–$C_7$ alkyl, cyanomethyl;
(b) $C_1$–$C_6$ alkoxy;
(c) benzyl, phenoxymethyl, p-methoxyphenylmethyl;
(d) 2-thienylmethyl, 3-thienylmethyl, 2-furylmethyl, 3-furylmethyl, 2-thiazolylmethyl, 5-tetrazolylmethyl, 1-tetrazolylmethyl;
(e) 1-protected hydroxybenzyl, 1-protected aminobenzyl, 1-protected amino(4-protected hydroxybenzyl).
$R_2$ is tert-butyl, p-methoxybenzyl or diphenylmethyl, and $R_3$ is another molecule of the identically substituted azetidinone alcohol moiety bonded to the opposite end of the disulfide group, or is phenyl or a mono-substituted phenyl, where the substituents are chloro, methoxy, methyl or acetoxy.

Illustrative of the preferred compounds of the invention, and hence the preferred group of substituents for the process of this invention include the following symmetrical azetidinone alcohol disulfide compounds:

4R,4′R bis[1-diphenylmethyl-2-N-3-methyl-4-ol-Z-but-2-ene-oate)-2-oxo-3S-phenylacetamido azetidine]disulfide, 4R,4′R bis[1-(p-methoxybenzyl 2-N-3-methyl-4-ol-Z-but-2-ene-oate)-2-oxo-3S-(2-(2-thienyl)acetamido)-azetidine]disulfide, 4R,4′R bis[1-(tert-butyl 2-N-3-methyl-4-ol-Z-but-2-ene-oate)-2-oxo-3S-(2-(2-thiazolyl)acetamido azetidine]-disulfide, 4R,4′R bis[1-(diphenylmethyl 2-N-3-methyl-4-ol-Z-but-2-ene-oate)-2-oxo-3S-(2-(1-tetrazolyl)acetamido)azetidine]disulfide, 4R,4′R bis[1-(p-methoxybenzyl 2-N-3-methyl-4-ol-Z-but-2-ene-oate)-2-oxo-3S-phenoxyacetamido azetidine]disulfide, 4R,4′R bis[1-(tert-butyl 2-N-3-methyl-4-ol-Z-but-2-ene-oate)-2-oxo-3S-(2-(2-furyl)acetamido)azetidine]disulfide, 4R,4′R bis[1-(diphenylmethyl 2-N-3-methyl-4-ol-Z-but-2-ene-oate)-2-oxo-3S-cyanoacetamido azetidine]disulfide, 4R,4′R bis[1-(p-methoxybenzyl 2-N-3-methyl-4-ol-Z-but-2-ene-oate)-2-oxo-3S-(2-benzylcarbonato-2-phenylacetamido azetidine]disulfide, 4R,4′R bis[1-(tert-butyl 2-N-3-methyl-4-ol-Z-but-2-ene-oate)-2-oxo-3S-(2-tert-butoxycarbonylamino-2-phenylacetamido) azetidine]disulfide, 4R,4′R bis[1-diphenylmethyl 2-N-3-methyl-4-ol-Z-but-2-ene-oate)-2-oxo-3S-(2-(tert-butoxycarbonylamino)-2-(4-benzylcarbonatophenyl)acetamido) azetidine]disulfide, 4R,4′R bis[1-diphenylmethyl 2-N-3-methyl-4-ol-Z-but-2-ene-oate)-2-oxo-3S-(2-benzyloxycarbonyl-2-phenylacetamido) azetidine]disulfide.

Preferred unsymmetrical disulfides of this invention include:

phenyl 4R[1-(diphenylmethyl 2-N-3-methyl-4-ol-Z-but-2-ene-oate)-2-oxo-3S-phenylacetamido azetidine]disulfide, p-methylphenyl 4R[1-(diphenylmethyl 2-N-3-methyl-4-ol-Z-but-2-ene-oate)-2-oxo-3S-phenylacetamido azetidine]disulfide, o-chlorophenyl 4R[1-(tert-butyl 2-N-3-methyl-4-ol-Z-but-2-ene-oate)-2-oxo-3S-phenylacetamido azetidine]disulfide, p-methoxyphenyl 4R[1-(p-methoxybenzyl 2-N-3-methyl-4-ol-Z-but-2-ene-oate)-2-oxo-3S-phenylacetamido azetidine]disulfide, p-acetoxyphenyl 4R[1-(diphenylmethyl 2-N-3-methyl-4-ol-Z-but-2-ene-oate)-2-oxo-3S-phenylacetamido azetidine]disulfide, phenyl 4R[1-(diphenylmethyl 2-N-3-methyl-4-ol-Z-but-2-ene-oate)-2-oxo-3S-phenoxyacetamido azetidine]disulfide, p-methylphenyl 4R[1-(diphenylmethyl 2-N-3-methyl-4-ol-Z-but-2-ene-oate)-2-oxa-3S-phenoxyacetamido azetidine]disulfide, p-chlorophenyl 4R[1-(tert-butyl 2-N-3-methyl-4-ol-Z-but-2-ene-oate)-2-oxo-3S-phenoxyacetamido azetidine]disulfide, o-methoxyphenyl 4R[1-(p-methoxybenzyl 2-N-3-methyl-4-ol-Z-but-2-ene-oate)-2-oxo-3S-phenoxyacetamido azetidine]disulfide, p-acetoxyphenyl 4R[1-(diphenylmethyl 2-N-3-methyl-4-ol-Z-but-2-ene-oate)-2-oxo-3S-phenoxyacetamido azetidine]disulfide, phenyl 4R[1-(diphenylmethyl 2-N-3-methyl-4-ol-Z-but-2-ene-oate)-2-oxo-3S-(2-(2-thienyl)acetamido)azetidine]disulfide, p-chlorophenyl 4R[1-(tert-butyl 2-N-3-methyl-4-ol-Z-but-2-ene-oate)-2-oxo-3S-(2-(2-thienyl)acetamido) acetidine]disulfide, m-chlorophenyl 4R[1-(p-methoxybenzyl 2-N-3-methyl-4-ol-Z-but-2-ene-oate)-2-oxo-3S-(2-(2-thiazolyl)acetamido) azetidine]disulfide, p-methoxy 4β[1-(diphenylmethyl 2-N-3-methyl-4-ol-Z-but-2-ene-oate)-2-oxo-3α-(2-(2-thiazolyl)acetamido) acetidine]disulfide, o-methoxy 4β[1-(tert-butyl 2-N-3-methyl-4-ol-Z-but-2-ene-oate)-2-oxo-3α-(2-(1-tetrazolyl)acetamido)azetidine]disulfide, p-acetoxyphenyl 4R[1-(p-methoxybenzyl 2-N-3-methyl-4-ol-Z-but-Z-ene-oate)-2-oxo-3S-(2-(1-tetrazolyl)acetamido) azetidine]disulfide, o-acetoxyphenyl 4R[1-(diphenylmethyl 2-N-3-methyl-4-ol-Z-but-2-ene-oate)-2-oxo-3S-(2-(2-furyl)acetamido) azetidine]disulfide, phenyl 4R[1-(tert-butyl 2-N-3-methyl-4-ol-Z-but-2-ene-oate)-2-oxo-3S-(2-(2-furyl)acetamido)azetidine]disulfide, phenyl 4R[1-(p-methoxybenzyl 2-N-3-methyl-4-ol-Z-but-2-ene-oate)-2-oxo-3S-cyanoacetamido azetidine]disulfide, p-chlorophenyl 4R[1-(diphenylmethyl 2-N-3-methyl-4-ol-Z-but-2-ene-oate)-2-oxo-3S-cyanoacetamido acetidine]disulfide, o-chlorophenyl 4R[1-(tert-butyl 2-N-3-methyl-4-ol-Z-but-2-ene-oate)-2-oxo-3S-(2-benzylcarbonato-2-phenylactamido azetidine]disulfide, p-methoxyphenyl 4R[1-(p-methoxybenzyl 2-N-3-methyl-4-ol-Z-but-2-ene-oate)-2-oxo-3S-(2-benzylcarbonato-2-phenylacetamido acetidine]disulfide, o-methoxybenzyl 4R[1-(diphenylmethyl 2-N-3-methyl-4-ol-Z-but-2-ene-oate)-2-oxo-3S-(2-tert-butoxycarbonylamino-2-phenylacetamido) azetidine]disulfide, p-methylphenyl 4R[1-(tert-butyl 2-N-3-methyl-4-ol-Z-but-2-ene-oate)-2-oxo-3S-(2-tert-butoxycarbonylamino-2-phenylacetamido) azetidine]disulfide, m-methylphenyl 4R[1-(p-methoxybenzyl 2-N-3-methyl-4-ol-Z-but-2-ene-oate)-2-oxo-3S-(2-(tert-butoxycarbonylamino)-2-(4-benzylcarbonatophenyl)acetamido azetidine]disulfide, p-acetoxyphenyl 4R[1-(diphenylmethyl 2-N-3-methyl-4-ol-Z-but-2-ene-oate)-2-oxo-3S-(2-(tert-butoxycarbonylamino)-2-(4-benzylcarbonatophenyl)acetamido) azetidine]disulfide, o-acetoxy 4β[1-(tert-butyl 2-N-3-methyl-4-ol-Z-but-2-ene-oate)-2-oxo-3α-(2-benzyloxycarbonyl-2-phenylacetamido) acetidine]disulfide and phenyl 4β[1-(p-methoxybenzyl 2-N-3-methyl-4-ol-Z-but-2-ene-oate)-2-oxo-3α-(2-benzyloxycarbonyl-2-phenylacetamido) acetidine]disulfide.

A more preferred group of azetidinone alcohol disulfide compounds of this invention are again represented by the following general formula

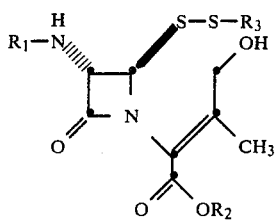

wherein R₁ is an acyl group of the formula

wherein R' is

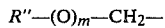

wherein R" is phenyl or substituted phenyl wherein the substituents are 1 or 2 halogens, protected hydroxy, cyano, trifluoromethyl, $C_1$–$C_4$ alkyl, $C_1$–$C_4$ alkoxy, protected carboxy, protected carboxymethyl, protected hydroxymethyl or protected aminomethyl; and m is 0 or 1, R₂ is tert-butyl, p-methoxybenzyl or diphenylmethyl and R₃ is another molecule of the identically substituted azetidinone alcohol moiety bonded to the opposite end of the disulfide group, or is phenyl or a mono-substituted phenyl, where the substituents are chloro, methoxy, methyl or acetoxy.

Illustrative of the more preferred compounds of this invention, and hence the more preferred group of substrates for the process of this invention, are the following symmetrical azetidinone alcohol disulfide compounds:

4R,4'R bis[1-(diphenylmethyl 2-N-3-methyl-4-ol-Z-but-2-ene-oate)-2-oxo-3S-phenylacetamido azetidine]disulfide, 4R,4'R bis[1-(tert-butyl 2-N-3-methyl-4-ol-Z-but-2-ene-oate)-2-oxo-3S-phenoxyacetamido azetidine]disulfide, 4R,4'R bis[1-(p-methoxybenzyl 2-N-3-methyl-4-ol-Z-but-2-ene-oate)-2-oxo-3S-(p-methylphenyl)acetamido azetidine]disulfide, 4R,4'R bis[1-(diphenylmethyl 2-N-3-methyl-4-ol-Z-but-2-ene-oate)-2-oxo-3S-(2-(p-methoxyphenyl)acetamido azetidine]disulfide, 4R,4'β bis[1-(tert-butyl 2-N-3-methyl-4-ol-Z-but-2-ene-oate)-2-oxo-3S-(2-(4-benzylcarbonatophenyl)acetamido) azetidine]disulfide, 4R,4'β bis[1-(p-methoxybenzyl 2-N-3-methyl-4-ol-Z-but-2-ene-oate)-2-oxa-3S-(4-chlorophenylacetamido) azetidine]disulfide, 4R,4'R bis[1-(diphenylmethyl 2-N-3-methyl-4-ol-Z-but-2-ene-oate)-2-oxo-3S-(2-chlorophenylacetamido) azetidine]disulfide, 4R,4'R bis[1-(tert-butyl 2-N-3-methyl-4-ol-Z-but-2-ene-oate)-2-oxo-3S-(4-trifluoromethylphenylacetamido) azetidine]disulfide, 4R,4'R bis[1-(diphenylmethyl 2-N-3-methyl-4-ol-Z-but-2-ene-oate)-2-oxo-3S-(2-(4-benzyloxycarbonylphenyl)acetamido) azetidine]disulfide, 4R,4'R bis[1-(tert-butyl 2-N-3-methyl-4-ol -Z-but-2-ene-oate)-2-oxo-3S-(2-(4-benzylcarbonatomethylphenyl)acetamido) azetidine]disulfide, 4R,4'R bis[1-(p-methoxybenzyl 2-N-3-methyl-4-ol-Z-but-2-ene-oate)-2-oxo-3S-(2-(4-benzyloxycarbonylmethylphenyl)acetamido)] azetidine]disulfide, 4R,4'R bis[1-(diphenylmethyl 2-N-3-methyl-4-ol-Z-but-2-ene-oate)-2-oxo-3S-(2-(4-tert-butoxycarbonylaminomethylphenyl)acetamido) azetidine]disulfide, and 4R,4'R bis[1-(tert-butyl 2-N-3-methyl-4-ol-Z-but-2-ene-oate)-2-oxo-3S-(2-(4-cyanophenyl)acetamido) azetidine]disulfide.

The following are illustrative of the more preferred unsymmetrical disulfides of this invention.

phenyl 4R[1-(diphenylmethyl 2-N-3-methyl-4-ol-Z-but-2-ene-oate)-2-oxo-3S-phenylacetamido azetidine]disulfide, p-methylphenyl 4R[1-(diphenylmethyl 2-N-3-methyl-4-ol-Z-but-2-ene-oate)-2-oxo-3S-phenylacetamido azetidine]disulfide, o-chlorophenyl 4R[1-(tert-butyl 2-N-3-methyl-4-ol-Z-but-2-ene-oate)-2-oxo-3S-phenylacetamido azetidine]disulfide, p-methoxyphenyl 4R[1-(p-methoxybenzyl 2-N-3-methyl-4-ol-Z-but-2-ene-oate)-2-oxo-3S-phenylacetamido azetidine]disulfide, p-acetoxyphenyl 4R[1-(diphenylmethyl 2-N-3-methyl-4-ol-Z-but-2-ene-oate)-2-oxo-3S-phenylacetamido azetidine]disulfide, phenyl 4R[1-(diphenylmethyl 2-N-3-methyl-4-ol-Z-but-2-ene-oate)-2-oxo-3S-phenoxyacetamido azetidine]disulfide, p-methylphenyl 4R[1-(diphenylmethyl 2-N-3-methyl-4-ol-Z-but-2-ene-oate)-2-oxo-3S-phenoxyacetamido azetidine]disulfide, p-chlorophenyl 4R[1-(tert-butyl 2-N-3-methyl-4-ol-Z-but-2-ene-oate)-2-oxo-3S-phenoxyacetamido azetidine]disulfide, o-methoxyphenyl 4R[1-(p-methoxybenzyl 2-N-3-methyl-4-ol-Z-but-2-ene-oate)-2-oxo-3S-phenoxyacetamido azetidine]disulfide, p-acetoxyphenyl 4R-[1-(diphenylmethyl 2-N-3-methyl-4-ol-Z-but-2-ene-oate)-2-oxo-3S-phenoxyacetamido azetidine]disulfide, phenyl 4R[1-diphenylmethyl 2-N-3-methyl-4-ol-Z-but-2-ene-oate)-2-oxo-3S-(2-(p-methylphenyl)acetamido) azetidine]disulfide, p-chlorophenyl 4R[1-(tert-butyl 2-N-3-methyl-4-ol-Z-but-2-ene-oate)-2-oxo-3S-(2-(p-methylphenyl))acetamido) azetidine]disulfide, m-chlorophenyl 4R[1-(p-methoxybenzyl 2-N-3-methyl-4-ol-Z-but-2-ene-oate)-2-oxo-3S-(2-(p-methoxyphenyl)acetamido) azetidine]disulfide, p-methoxyphenyl 4R-[1-(diphenylmethyl 2-N-3-methyl-4-ol-Z-but-2-ene-oate)-2-oxo-3S-(2-(p-methoxyphenyl)acetamido) azetidine]disulfide, o-methoxyphenyl 4R[1-(tert-butyl 2-N-3-methyl-4-ol-Z-but-2-ene-oate)-2-oxo-3S-(2-(4-benzyloxycarbonylphenyl)acetamido) azetidine]disulfide, p-methylphenyl 4R[1-(p-methoxybenzyl 2-N-3-methyl-4-ol-Z-but-2-ene-oate)-2-oxo-3S-(2-(4-benzyloxycarbonylphenyl)acetamido) azetidine]disulfide, o-methylphenyl 4R[1-(diphenylmethyl 2-N-3-methyl-4-ol-Z-but-2-ene-oate)-2-oxo-3S-(4-chlorophenylacetamido) azetidine]disulfide, p-acetoxyphenyl 4R[1-(tert-butyl 2-N-3-methyl-4-ol-Z-but-2-ene-oate)-2-oxo-3S-(4-chlorophenylacetamido) azetidine]disulfide, o-acetoxyphenyl 4R[1-(p-methoxybenzyl 2-N-3-methyl-4-ol-Z-but-2-ene-oate)-2-oxo-3S-(2-chlorophenylacetamido) azetidine]disulfide, phenyl 4R[1-(diphenylmethyl 2-N-3-methyl-4-ol-Z-but-2-ene-oate)-2-oxo-3S-(2-chlorophenylacetamido) azetidine]disulfide, phenyl 4R[1-(tert-butyl 2-N-3-methyl-4-ol-Z-but-2-ene-oate)-2-oxo-3S-(4-trifluoromethylphenylacetamido) azetidine]disulfide, p-chlorophenyl 4R[1-(p-methoxybenzyl 2-N-3-methyl-4-ol-Z-but-2-ene-oate)-2-oxo-3S-(4-trifluoromethylphenylacetamido) azetidine]disulfide, o-chlorophenyl 4R[1-(diphenylmethyl 2-N-3-methyl-4-ol-Z-but-2-ene-oate)-2-oxo-3S-(2-(4-benzyloxycarbonylphenyl)acetamido) azetidine]disulfide, p-methoxyphenyl 4R[1-(tert-butyl 2-N-3-methyl-4-ol-Z-but-2-ene-oate)-2-oxo-3S-(2-(4-benzyloxycarbonylphenyl)acetamido) azetidine]disulfide, o-methoxyphenyl 4R[1-(p-methoxybenzyl 2-N-3-methyl-4-ol-Z-but-2-ene-oate)-2-oxo-3S-(2-(4-tert-butoxycarbonylaminomethylphenyl)acetamido) azetidine]disulfide, p-methylphenyl 4R[1-(diphenylmethyl 2-N-3-methyl-4-ol-Z-but-2-ene-oate)-2-oxo-3S-(2-(4-tert-butoxycarbonylaminomethylphenyl)acetamido azetidine]disulfide, m-methylphenyl 4R[1-(tert-butyl 2-N-3-methyl-4-ol-Z-but-2-ene-oate)-2-oxo-3S-(2-(4-cyanophenyl)acetamido) azetidine]disulfide and p-acetoxyphenyl 4R[1-(p-methoxybenzyl 2-N-3-methyl-4-ol-Z-but-2-ene-oate)-2-oxo-3S-(2-(4-cyanophenyl)acetamido) azetidine]disulfide.

The starting material utilized in the process of this invention is synthesized by first epimerizing the C-6 side chain of a penicillin sulfoxide from the β to the α conformation, followed by the rearrangement of the 6α-acylamino-penicillin sulfoxide to the corresponding 7α-acylamino-3-methyl cephalosporin. The next step involves the 2α-alkoxylation of the above cephalosporin. The final step in the synthesis of the starting material for this invention involves the formation of an azetidinone disulfide aldehyde from the 7α-acylamino-2α-alkoxy-3-methyl cephalosporin. Specifically, in the synthesis of the starting material for the process of this invention, the epimerization at C-6 of the 6β-acylaminopenicillanate-1-sulfoxide, represented by the following scheme:

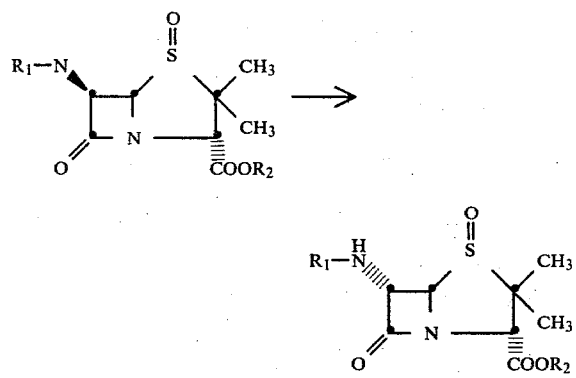

is a process well known to those skilled in the art. See, for example, Ramsay and Stoodley, *Chemical Communications*, 1971, 450, Koppel, *Tetrahedron Letters*, 1973, 4233, Stoodley, U.S. Pat. No. 3,853,848, Clair et al, *J.C.S. Perkin Transactions* I, 937 (1973), and Barton et al, *J.C.S. Perkin Transactions* I, 599, 1973. The preferred method of epimerization at the C-6 position involves reacting the naturally occurring 6β-acylamino compound with one mole of trimethylsilyl chloride in methylene chloride at between 0° C. and ambient temperature, cooling the mixture to 0° C., and adding dropwise 2 equivalents of triethylamine. The product can be purified by standard extraction and recrystallization techniques. The desired α-isomer can be isolated by dissolving the isomer mixture from the reaction mixture in a minimum quantity of ethyl acetate and adding a few crystals of the β-isomer to facilitate crystallization of the β-isomer. The β-isomer crystals are filtered, resulting in a filtrate containing substantially pure (approximately 90%) α-isomer of the penicillinate, which α-isomer can be isolated by evaporating the filtrate to dryness.

The preferred procedure of C-6 epimerization is described by Blaszczak in copending application Ser. No. 138,022, entitled "Process for Penicillin Epimerization", filed this even date.

The rearrangement of the 6α-acylaminopenicillinate-1-sulfoxide to the corresponding 7α-acylamino-3-methyl-3-cephem-4-carboxylate, represented by the following general formula:

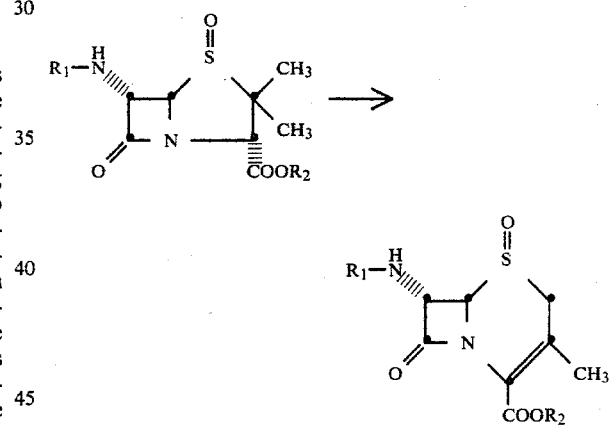

is analogous to a procedure also well known to those skilled in the art. Although several variations of the method are available to effect this rearrangement, the preferred method involves reacting the 6α-acylaminopenicillinate-1-sulfoxide with N,O-bis(trimethylsilyl)acetamide (BSA) and α-picoline.HBr in dried dioxane at reflux temperatures. The organic products of the reaction are then extracted into ethyl acetate, and the extract is treated with neat pyridine. Pure 7α-acylamino-3-methyl-3-cephem-4-carboxylate can be obtained by recrystallization.

The procedure for the above rearrangement step was adapted from one described by Verweij et al., in U.S. Pat. No. 4,003,894.

The next step in the general reaction scheme for preparing the starting material of this invention involves an α-alkoxylation at the C-2 position of the cephem moiety. This reaction is represented in the following general formula:

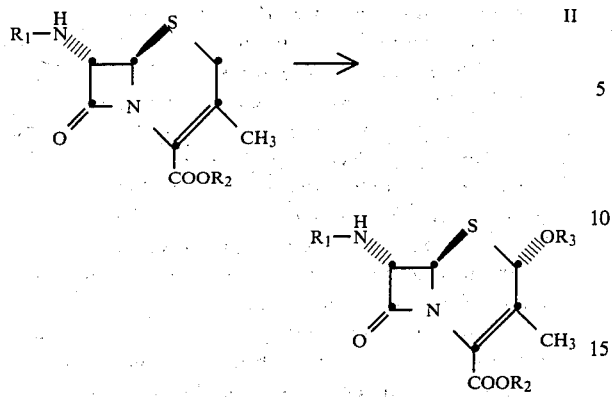

As with the above two steps in the synthesis of this starting material, the 2α-alkoxylation reaction involved at this stage of the synthesis is analogous to procedures well known to those skilled in the art; see, for example, D. O. Spry, *Tetrahedron Letters*, 3717 (1972); A. Yoshida, S. Oida, and E. Ohki, *Chemical and Pharmaceutical Bulletin of Japan* (Tokyo), 23, 2507 and 2518 (1975); ibid., 24 362 (1976); ibid. 25, 2082 (1977); C. O. Kim and P. A. McGregor, *Tetrahedron Letters*, 409 (1978). Although the aforementioned references describe various methods of 2α-alkoxylation for 7β-isomers of cephalosporins, the preferred method for the conversion of 7α-acylamino-3-methyl-3-cephem-4-carboxylate to its corresponding 2α-alkoxy analog comprises the addition of N-chlorosuccinimide to a solution of the substrate cephem compound dissolved in an appropriate alcohol and methylene chloride at room temperature. The desired 2α-alkoxy product can then be isolated by standard crystallization and chromatography techniques.

The final step in the synthesis of the starting materials for this invention involves converting the 7α-acylamino-2α-alkoxy-3-methyl cephalosporin to an azetidinone aldehyde disulfide.

The disulfide formation step in the above general reaction scheme can be accomplished in one of two methods, with each method yielding a different product. One method of disulfide formation, represented by the following general formula,

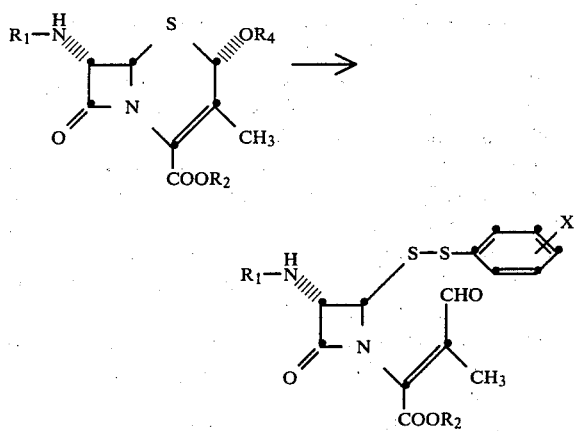

entails adding the 7α-acylamino-2α-alkoxy-3-methyl-3-cephem-4-carboxylate compound to a methylene chloride solution of arylsulfenyl chloride at 0° C. The desired aryl 4β[1-(protected carboxy 2-N-3-methyl-4-al-Z-but-2-ene-oate)-2-oxo-3α-acylamino azetidine]disulfide can be reduced at this point to give the unsymmetrical azetidinone alcohol disulfide compounds of this invention, or may be further purified by conventional chromatographic techniques before submitting these unsymmetrical azetidinone aldehyde disulfides to reduction. This method for disulfide formation is described by Kukolja and Pfeil in copending application Ser. No. 137,861, entitled "Unsymmetrical Azetidinone Aldehyde Disulfide and Process", now U.S. Pat. No. 4,302,391, filed this even date.

The alternate method for disulfide formation represented by the following general formula:

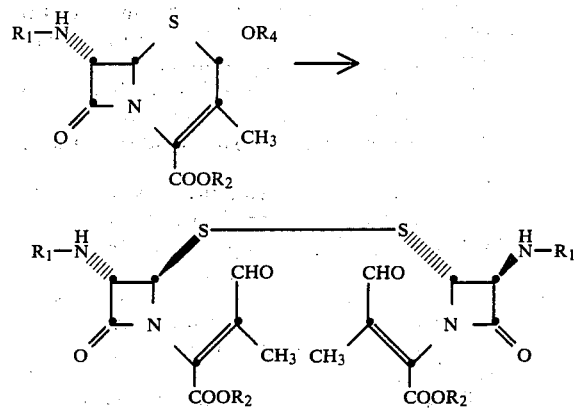

involves adding N-chlorosuccinimide to a methylene chloride solution of the appropriate 7α-acylamino-2α-alkoxy-3-methyl-3-cephem-4-carboxylate compound at 0° C. This solution is then added to an aqueous suspension of mercury dichloride and cadmium carbonate at room temperature. This method of disulfide formation produces a symmetrical disulfide compound that has identically substituted azetidinone moieties bonded to either end of the disulfide linkage, in contrast with the disulfide formation method employing an arylsulfenyl chloride, which produces an unsymmetrical azetidinone disulfide compound having an aryl group bonded to one end and an azetidinone moiety bonded to the other end of the disulfide group. The 4R,4′R bis[1-(protected carboxy [2-N-3-methyl-4-al-Z-but-2-ene-oate)-2-oxo]-3S-acylamino azetidine]disulfide produced in the former method can be reduced at this point to give the symmetrical azetidinone disulfide alcohol compounds of this invention, or may be further purified by conventional chromatographic techniques before submitting these symmetrical azetidinone aldehyde disulfides to reduction. This method of disulfide formation which produce symmetrical azetidinone aldehyde disulfide compounds is described in Kukolja and Pfeil in copending application Ser. No. 138,023, entitled "Symmetrical Azetidinone Aldehyde Disulfide and Process", now U.S. Pat. No. 4,293,495, filed this even date.

As indicated in the present application both the symmetrical and unsymmetrical azetidinone aldehyde disulfide compounds are precursors to the compounds of this invention.

The compounds of this invention are intermediates useful in the preparation of a particular class of biologically active 1-oxa β-lactam compounds. These intermediate compounds are cyclized by the process of this invention to the desired 7α-acylamino-3-methyl 1-oxa β-lactam. This conversion of the azetidinone alcohol disulfide compounds to a 1-oxa β-lactam and the remaining steps necessary to synthesize the desired 7β-acylamino-7α-methoxy-3-methyl 1-oxa β-lactam antibiotic compounds is accomplished by first 7α-methoxylating the 7α-acylamino 1-oxa β-lactam compounds obtained from the process of this invention, then by removing the protecting group on the C-4 carboxylic acid function to give the desired 7β-acylamino-7α-methoxy 1-oxa β-lactam acid antibiotic compounds.

As mentioned above, the first step in the synthesis of the desired antibiotic 1-oxa β-lactam compounds involves converting the 7α-acylamino-3-methyl 1-oxa β-lactam compound obtained from the process of this invention to the corresponding 7β-acylamino-7α-methoxy-3-methyl 1-oxa β-lactam by reacting the 7α-acylamino substrate with lithium methoxide and tert-butyl hypochlorite. This reaction is represented generally by the following formula;

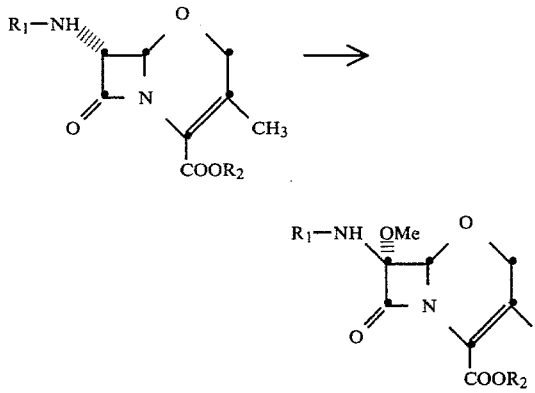

The reaction entails the addition of the 7α-acylamino 1-oxa β-lactam to a suspension of lithium methoxide in dry tetrahydrofuran in an inert atmosphere followed by addition of tert-butyl hypochlorite to the solution to initiate the methoxylation. Once the reaction has reached completion, the reaction is quenched with trimethylphosphite and glacial acetic acid. The desired product can be isolated and purified with conventional liquid-liquid extraction techniques.

The conversion of the 7α-acylamino-3-methyl 1-oxa β-lactam to the 7β-acylamino-7α-methoxy-3-methyl 1-oxa β-lactam is carried out in a manner analogous to that of G. A. Koppel and R. E. Koehler, *Journal of the American Chemical Society*, 95, 2403 (1973).

The final step in the synthesis of a 1-oxa β-lactam compound from the claimed symmetrical and unsymmetrical azetidinone alcohol disulfide compound is to remove the carboxylic acid protecting group from the 7β-acylamino-7α-methoxy-3-methyl 1-oxa β-lactam ester, as shown below;

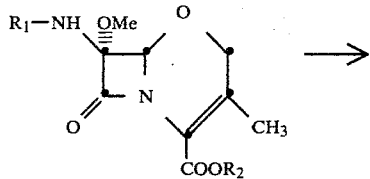

-continued

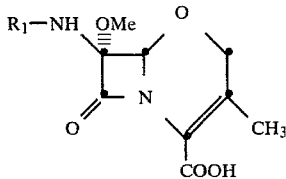

The deprotection step is well known to anyone skilled in the art. For example, to remove the diphenylmethyl carboxylic acid protecting group, the substrate diphenylmethyl carboxylate is dissolved in anisole and then treated with trifluoroacetic acid. The resultant 7β-acylamino-7α-methoxy-3-methyl 1-oxa β-lactam acids are antibiotics. Further examples of this deprotection step can be found in U.S. Pat. No. 4,138,486.

The following Examples (1-3) are provided to further illustrate this invention. Preparations 1 through 3 demonstrate a method of synthesizing the starting materials for the process of the invention, and preparations 4-8 demonstrate one way of converting the claimed compounds of this invention into biologically active 1-oxa β-lactam compounds. It is not intended that this invention be limited in scope by reason of any of the preparations or examples. In the following preparations and examples infrared absorption spectra, nuclear magnetic resonance spectra, ultraviolet absorption spectra and optical rotation spectra are abbreviated i.r., n.m.r., u.v. and o.r., respectively. Only the i.r. absorption maxima or peaks attributable to the carbonyl function of the β-lactam ring are reported. The nuclear magnetic resonance spectra were obtained on a Varian Associates T-60 Spectrometer using tetramethylsilane as the reference standard. The chemical shifts are expressed in δ values in parts per million (ppm) and coupling constants (J) are expressed in Hz.

EXAMPLE 1

4R,4′R Bis[1-(diphenylmethyl 2-N-3-methyl-4-ol-Z-but-2-ene-oate)-2-oxo-3S-phenylacetamido azetidine]disulfide.

4R,4′R Bis[1-(diphenylmethyl 2-N-3-methyl-4-al-Z-but-2-ene-oate)-2-oxo-3S-phenylacetamido azetidine]disulfide (524 mg, 0.51 mmol) was dissolved in a solution of 10 ml tetrahydrofuran (THF) and 1 ml of water. The pH of this solution was adjusted to 3.5 with a 1 molar THF solution of sodium hydroxide. Sodium cyanoborohydride (63 mg, 1.0 mmol) was added to the solution and the reaction mixture was stirred at room temperature for 0.5 hour, during which time the pH of the solution was maintained between 3.2 and 3.6 with additions of a solution of 3 ml of 1 molar hydrochloric acid and 3 ml of acetic acid in 20 ml of THF. At the end of 0.5 hour, the reaction solution was poured into a solution composed of 75 ml of saturated sodium chloride solution and 50 ml of ethyl acetate, and this resultant mixture was stirred for ten minutes. The layers were then separated and the ethyl acetate layer was washed sequentially with water (1X), saturated sodium bicarbonate (1X), water (1X), saturated sodium chloride (1X), and was then dried over magnesium sulfate, filtered and evaporated to dryness. The resulting colorless foam was the product, 4R,4′R bis[1-(diphenylmethyl 2-N-3-methyl-4-ol-Z-but-2-ene-oate)-2-oxo-3S-phenylacetamido azetidine]disulfide (500 mg.): n.m.r. (CDCl₃) δ2.18 (s, 3, CH₃), 3.48 (s, 2, CH₂Ph), 3.93 and 4.20 (ABq, J=13 Hz, 2, CH$_2$OH), 4.87 (dd, J=2 and 9 Hz, 1, C$_3$—) 5.04 (d, J=2 Hz, 1, C$_4$—H), 6.86 (s, 1, CHPh$_2$), and 7.28 (br. s, 16, aromatic H and N—H).

EXAMPLE 2 p-Methylphenyl 4R[1-(diphenylmethyl 2-N-3-methyl-4-ol-Z-but-2-ene-oate)-2-oxo-3S-phenylacetamido azetidine]disulfide p-Methylphenyl 4R[1-(diphenylmethyl 2-N-3-methyl-4-al-Z-but-2-ene-oate)-2-oxo-3S-phenylacetamido azetidine]disulfide (766 mg, 1.2 mmol) was dissolved in 20 ml of tetrahydrofuran (THF) followed by the addition of 2 ml of water. The pH of this solution was adjusted to 3.5 by the addition of a 1 molar THF solution of sodium hydroxide. Sodium cyanoborohydride (83 mg, 1.32 mmol) was added to the reaction solution, and the solution was stirred at ambient temperature for 2 hours, all the while maintaining the pH of the solution between 3.2 and 3.6 by additions of an acidic solution (3 ml. of 1 molar hydrochloric acid and 3 ml of acetic acid in 20 ml of THF.). At the end of two hours the reaction solution was poured into a solution consisting of 75 ml of saturated sodium chloride solution and 50 ml of ethyl acetate, and the resulting suspension was stirred for ten minutes. The ethyl acetate layer from this solution was separated and washed in sequence with water (1×), saturated sodium bicarbonate solution (1×), water (1×), saturated sodium chloride solution (1×), dried over magnesium sulfate, filtered and evaporated to dryness. The solid remaining after evaporation was absorbed onto 3.5 grams of silica, and chromatographed on 10 grams of silica using, in sequence, 100 ml of toluene, 200 ml of 5% ethyl acetate toluene, 150 ml of 10% ethyl acetate toluene and 100 ml each of 15%, 20%, 25% and 30% ethyl acetate in toluene. The final fraction collected contained the desired alcohol p-methylphenyl 4R[1-(diphenylmethyl 2-N-3-methyl-4-ol-Z-but-2-ene-oate)-2-oxo-3S-phenylacetamido azetidine]disulfide. (116 mg, 15% yield) n.m.r. (CDCl$_3$) δ2.00 (s, 3CH$_3$), 2.30 (s, 3, toluyl —CH$_3$), 2.88 (br. s, 1, OH), 3.41, 3.90 (ABq, J=13 Hz, 2, CH$_2$OH), 3.47 (s, 2, CH$_2$Ph), 4.62 (dd, J=3 and 8 Hz, 1, C$_3$—H) 5.17 (d, J=3 Hz, 1, C$_4$—H), 6.32 (d, J=8 Hz, 1, N—H), 6.97 (s, 1, CHPh$_2$), 7.25 (m, 19, aromatic protons).

EXAMPLE 3

Phenyl 4R[1-(diphenylmethyl 2-N-3-methyl-4-ol-Z-but-2-ene-oate)-2-oxo-3S-phenylacetamido azetidine]disulfide Phenyl 4R[1-(diphenylmethyl-2-N-3-methyl-4-al-Z-but-2-ene-oate)-2-oxo-3S-phenylacetamido azetidine]disulfide is dissolved in tetrahydrofuran (THF) then a small amount of water is added. The pH of this solution is adjusted to 3.5 by the addition of a 1 molar THF solution of sodium hydroxide. Sodium cyanoborohydride is added to the reaction solution, and the solution is stirred at ambient temperature for 2 hours, all the while maintaining the pH of the solution between 3.2 and 3.6 by additions of an acidic solution (3 ml of 1 molar hydrochloric acid and 3 ml of acetic acid in 20 ml of THF). At the end of two hours the reaction solution is poured into a solution consisting of saturated sodium chloride solution and ethyl acetate, and the resultant suspension is stirred for ten minutes. The ethyl acetate layer from this solution is separated and is washed in sequence with water (1×), saturated sodium bicarbonate solution (1×), then dried over magnesium sulfate, filtered, and evaporated to dryness. The solid remaining after evaporation is chromatographed on silica gel using, in turn, toluene, 5%, 10%, 15%, 20%, 25% and 30% ethyl acetate in toluene.

EXAMPLE 4

7α-Phenylacetamido-3-methyl 1-oxa β-lactam ester

Bis(trifluoroacetato)mercury(II) (1.48 g, 3.4 mmol) and 4R,4'R bis[1-(diphenylmethy 2-N-3-methyl-4-ol-Z-but-2-ene-oate)-2-oxo-3S-phenylacetamido azetidine]disulfide (866 mg, 0.84 mmol) were dissolved under positive pressure of nitrogen in 16 ml. of dried acetonitrile. The reaction mixture was stirred for 0.5 hour at ambient temperature, at the end of which time it was filtered and the filtrate was taken to dryness. The resulting orange foam was dissolved in ethyl acetate and the ethyl acetate solution was washed with water (1×), saturated sodium chloride solution (1×), and then with a sodium chloride solution until the wash water was neutral. The ethyl acetate layer was filtered through a sintered glass funnel, dried over magnesium sulfate, filtered, and evaporated to dryness, yielding a dark orange foam (773 mg). This foam was recrystallized from an acetone/cyclohexane mixture and subsequent filtration of this mixture isolated pure crystals of the desired product, diphenylmethyl 7α-phenylacetamido-3-methyl 1-oxa β-lactam ester (65 mg). The filtrate from the above recrystallization was combined with the filtrate from another experiment done analogous to the above procedure, and this combined filtrate was chromatographed on silica gel eluting with 20% ethyl acetate in toluene to give more of the desired diphenylmethyl 7α-phenylacetamido-3-methyl 1-oxa β-lactam ester (mp 190°-191°), i.r. (CHCl$_3$) 1780 cm$^{-1}$; n.m.r. (d$_6$-acetone) δ1.93 (s, 3, CH$_3$), 3.6 (s, 2, CH$_2$Ph), 4.35 (br, s, 2, C$_3$—H), 4.73 (dd, J=1.5 and 9 Hz, 1, C$_7$—H), 4.99 (d, J=1.5 Hz, 1, C$_6$—H), 6.89 (s, 1, CHPh$_2$), and 7.3 L (m, 16, aromatic H and N—H); mass spectrum, m/e 406; u.v. λ$_{max}$ 263 nm (ε=6,072).

EXAMPLE 5

7α-Phenylacetamido-3-methyl 1-oxa β-lactam ester

Triphenylphosphine (278 mg, 1.06 mmol) and 4R,4'R bis[1-(diphenylmethyl 2-N-3-methyl-4-ol-Z-but-2-ene-oate)-2-oxo-3S-phenylacetamido azetidine]disulfide (464 mg, 0.52 mmol) were combined in 10 ml of dry 1,2-dichloroethane. The solution was refluxed for seventy minutes, after which time it was evaporated to dryness. The resulting yellow oil was chromatographed on 15 grams of silica gel using 1:1 ethyl acetate/hexane plus ½% acetic acid as the eluant. The pure product, diphenylmethyl 7α-phenylacetamido-3-methyl 1-oxa β-lactam (67 mg), possessed the same physical properties as the product compound in Example 4.

EXAMPLE 6

7α-Phenylacetamido-3-methyl 1-oxa β-lactam ester

The following reaction was carried out in an inert atmosphere (N$_2$) until after evaporation of the reaction solution. p-Methylphenyl 4R[1-(diphenylmethyl 2-N-3-methyl-4-ol-Z-but-2-ene-oate)-2-oxo-3S-phenylacetamido azetidine]disulfide (0.1 g, 0.16 mmol) was dissolved in 5 ml of dried acetonitrile. Bis(trifluoroacetato)mercury(II) (136 mg, 0.32 mmol) was added to the reaction solution and the solution was stirred at ambient temperature for 0.5 hour, during which time the color of the reaction solution changed from yellow to orange. The solution was evaporated to dryness, and the resulting solid was dissolved in ethyl acetate. This ethyl acetate solution was washed with water (1×), sodium bicarbonate solution (2×), sodium chloride solution (1×), dried over magnesium sulfate, filtered then evaporated to dryness. The resultant solid was chromatographed on a preparative-scale thin layer chromatography plate using a 1:1 solution of ethyl acetate/hexane as the eluant, yielding the pure 7α-phenylacetamido-3-methyl 1-oxa β-lactam ester compound (37 mg, 49% yield) which possessed the same physical properties as the product compound in Example 4.

EXAMPLE 7

7α-Phenylacetamido-3-methyl 1-oxa β-lactam ester.

Triphenylphosphine and p-methylphenyl 4R-[1-(diphenylmethyl 2-N-3-methyl-4-ol-Z-but-2-ene-oate)-2-oxo-3S-phenylacetamido azetidine]disulfide are combined in dry 1,2-dichloroethane. The solution is refluxed for seventy minutes, after which time it is evaporated to dryness. The resultant crude 7α-phenylacetamido-3-methyl 1-oxa β-lactam diphenylmethyl ester is chromatographed on silica gel using an equal volume mixture of ethyl acetate and hexane plus ½% acetic acid as the eluant.

EXAMPLE 8

7α-Phenylacetamido-3-methyl 1-oxa β-lactam diphenylmethyl ester

The following reaction is carried out in an inert atmosphere until after evaporation of the reaction solution. Phenyl 4R[1-(diphenylmethyl 2-N-3-methyl-4-ol-Z-but-2-ene-oate)-2-oxo-3S-phenylacetamido azetidine]disulfide is dissolved in dried acetonitrile. Bis(trifluoroacetato)mercury(II) is added to the reaction solution and the solution is stirred at ambient temperature for 0.5 hour. The solution is evaporated to dryness, and the resultant solid is dissolved in ethyl acetate. This ethyl acetate solution is washed with water (1×), sodium bicarbonate solution (2×), sodium chloride solution (1×), is dried over magnesium sulfate, is filtered then is evaporated to dryness. The resultant solid is chromatographed on a preparatory-scale thin layer chromatography plate using a 1:1 solution of ethyl acetate/hexane as the eluant.

EXAMPLE 9

7α-Phenylacetamido-3-methyl 1-oxa β-lactam diphenylmethyl ester

Triphenylphosphine and phenyl 4R[1-(diphenylmethyl 2-N-3-methyl-4-ol-Z-but-2-ene-oate)-2-oxo-3S-phenylacetamido azetidine]disulfide is combined in dry 1,2-dichloroethane. The solution is refluxed for seventy minutes, after which time it is evaporated to dryness. The resultant crude 7α-phenylacetamido-3-methyl 1-oxa β-lactam diphenylmethyl ester is chromatographed on silica gel using an equal volume mixture of ethyl acetate and hexane plus ½% acetic acid as the eluant.

PREPARATION 1

Benzyl 6α-phenylacetamidopenicillanate-1-sulfoxide

Benzyl 6β-phenylacetamidopenicillanate-1-sulfoxide (8.80 g, 20 mmol) was dissolved in 17 ml of methylene chloride under a positive nitrogen pressure, and the resultant solution was cooled to 2° C. in an ice/water bath. Triethylamine (6.1 ml, 43.8 mmol) was added to the cooled solution, which resulted in the precipitation of the penicillinate. Thirteen more ml of methylene chloride were added to the solution to dissolve the penicillinate, followed by the addition of chlorotrimethylsilane (2.8 ml, 22 mmol). The reaction solution was stirred for 1 hour at 0° C., allowed to warm to ambient temperature and stirred for 1.5 hours longer, at the end of which time more chlorotrimethylsilane (1 ml, 7.86 mmol) was added and the stirring was continued for an additional 45 minutes. After cooling the reaction mixture to 4° C., acetic acid (3 ml, 52 mmol) was added dropwise, followed by addition of methylene chloride (20 ml). The reaction solution was then washed with 1 molar hydrochloric acid (3×) and with a saturated sodium bicarbonate solution (2×). The layers were separated, and the water layer was extracted with methylene chloride. The methylene chloride layers were combined, washed with a saturated sodium chloride solution (1×) then dried over magnesium sulfate, filtered and evaporated to dryness. The resultant off-white foam (8.3 g) was recrystallized from a 1:1 mixture of ethyl acetate/cyclohexane. Five grams of the crystallized product was dissolved in 13 ml of ethyl acetate, and seeded with benzyl 6β-phenylacetamidopenicillanate-1-sulfoxide crystals, to yield white crystals of the 6β-isomer of the penicillanate (760 mg). The crystals of the 6β-isomer of the penicillanate of benzyl 6-phenylacetamidopenicillanate-1-sulfoxide were filtered off and the filtrate yielded predominately pure (approximately 90%) 6α-isomer of benzyl 6-phenylacetamidopenicillanate-1-sulfoxide. (4.06 g, 46% yield). n.m.r. (d$_5$-pyridine) δ1.13, 1.62 (s, 6, C(CH$_3$)$_2$, 3.78 (s, 2, COCH$_2$Ph), 4.92 (s, 1, C$_3$—H), 5.22 (br. s, 2, CO$_2$CH$_2$Ph), 5.52 (d, J=2 Hz, 1, C$_5$—H), 5.88 (dd, J=2 and 8 Hz, 1, C$_6$—H), 7.33 (m, 10, aromatic), 10.13 (d, J=8 Hz, 1, NH).

PREPARATION 2

Benzyl 7α-phenylacetamido-3-methyl-3-cephem-4-carboxylate

To a solution of benzyl 6α-phenylacetamidopenicillanate-1-sulfoxide (31.4 g, 71.6 mmole) in dried dioxane (500 ml) was added N,O-bis[trimethylsilyl]acetamide (BSA) (39 ml, 158 mmole) and 58 ml of an α-picoline.HBr solution (1.23 M in CH$_2$Cl$_2$, 71.6 mmol). This reaction mixture was refluxed for 5 hours, during which time the color of the reaction solution color changed from yellow to brown. The reaction solution was cooled to ambient temperature and poured into a stirring mixture of 1:1 ethyl acetate/ice water. The layers were separated and the ethyl acetate layer was washed sequentially with saturated sodium chloride solution (1×), 1 molar hydrochloric acid (4×), saturated sodium bicarbonate solution (1×), and again with saturated sodium chloride solution (2×). The ethyl acetate layer was then dried over magnesium sulfate, filtered, evaporated to dryness, and treated with neat pyridine (10 ml, 0.12 mole) for 1 hour. The pyridine solution was taken up in methylene chloride and washed first with 1 molar hydrochloric acid several times, then with brine solution (1×). The extract was dried over magnesium sulfate, filtered and evaporated to dryness. The resultant crude product was recrystallized by dissolution in a 7:1 ethyl acetate:cyclohexane solution and addition of a few seed crystals of the title product. Two crops of crystals were collected and gave a combined yield of 8.70 grams (29% yield) of substantially pure 7α-phenylacetamido-3-methyl-3-cephem-4-carboxylate (m.p. 169°–170° C.); i.r. (CHCl$_3$) 1773 cm$^{-1}$; n.m.r. (CDCl$_3$) δ2.00 (s, 3, CH$_3$), 3.10, 3.37 (ABq, J=15 Hz, 2, C$_2$—H), 3.53 (s, 2, COCH$_2$Ph), 4.55 (d, J=2 Hz, 1, C$_6$—H), 4.85 (dd, J=2 and 8 Hz, 1, C$_7$—H), 5.10 (s, 2, CO$_2$CH$_2$Ph), 6.98 (d, J=8 Hz, 1, NH), 7.27 (s, 5, aromatic protons) and 7.35 (s, 5, aromatic protons); u.v. (CHCl$_3$) λ$_{max}$ 264 nm (ε=8,210), o.r. [α]$_D^{25}$ +46.9°; mass spectrum, m/e 422.

Analysis: Calculated for C$_{23}$H$_{22}$N$_2$O$_3$S: C, 65.38; H, 5.25; N, 6.63; O, 15.15; S, B 7.59. Found: C, 65.25; H, 5.09; N, 6.63; O, 14.88; S, 7.44.

PREPARATION 3

Diphenylmethyl 7α-phenylacetamido-2α-methoxy-3-methyl-3-cephem-4-carboxylate.

To a solution of diphenylmethyl 7α-phenylacetamido-3-methyl-3-cephem-4-carboxylate (2.88 g, 5.8 mmole) in 40 ml of methanol and 60 ml of methylene chloride, was added N-chlorosuccinimide (882 mg, 6.6 mmol) and the mixture was stirred for 90 minutes at room temperature. The reaction solution was then washed with brine (2×) and dried over magnesium sulfate, filtered, and the solvent was evaporated under reduced pressure. The resultant yellow foam (2.84 g) was chromatographed over 100 grams of silica gel employing 10–15% of ethyl acetate in toluene as the eluting solvent. The first fraction to elute from the column was the desired 2α-methoxy cephem compound which was subsequently recrystallized from a mixture of ethyl acetate and cyclohexane to give pure diphenylmethyl 7α-phenylacetamido-2α-methoxy-3-methyl-3-cephem-4-carboxylate. (638 mg, 21% yield) (mp 144°–145° C.) i.r. (CHCl$_3$) 1780, 1725 and 1680 cm$^{-1}$; n.m.r. (CDCl$_3$) δ1.95 (s, 3, CH$_3$) 3.35 (s, 3, OCH$_3$), 3.45 (s, 2, CH$_2$Ph), 4.60 (s, 1, C$_2$—H), 4.70 (d, J=2 and 8 Hz, 1, C$_7$—H), 4.85 (d, J=2 Hz, 1, C$_6$—H), 6.95 (s, 1, CH$_2$Ph), 7.3 (m, 16, aromatic H and N—H); u.v. (CHCl$_3$) λ$_{max}$ 264 nm (ε=9726).

Analysis: Calculated for C$_{30}$H$_{28}$N$_2$O$_5$S: C, 68.16; H, 5.34; N, 5.30; S, 6.07. Found: C, 68.36; H, 5.33; N, 5.29; S, 5.90.

PREPARATION 4

4R,4'R bis[1-(benzyl 2-N-3-methyl-4-al-Z-but-2-ene-oate)-2-oxo-3S-phenylacetamido azetidine]disulfide.

To a solution of diphenylmethyl 7α-(2-phenylacetamido)-2α-methoxy-3-methyl-3-cephem-4-carboxylate (1.6 g, 3.5 mmol) in 50 ml of methylene chloride at 0° C. was added N-chlorosuccinimide (0.49 g, 3.64 mmol). The solution was stirred for 15 minutes, then was added to a rapidly stirring suspension of mercury dichloride (2.9 g, 10.6 mmol) and cadmium carbonate (3.78 g, 22 mmol) in 50 ml of water. The mixture was stirred at ambient temperature for 30 minutes, and filtered through pre-washed Celite. The methylene chloride was then separated and evaporated to dryness. The product was taken up in ethyl acetate and the ethyl acetate solution was washed with water (5×) then with saturated sodium chloride solution (1×) and subsequently dried over magnesium sulfate and filtered. Evaporation to dryness gave crude product (1.5 g, 99% yield) of which 800 mg was chromatographed on 15 grams of silica gel using 1:1 ethyl acetate:hexane as the eluant. The product, 4R,4'R bis[1-(benzyl 2-N-3-methyl-4-al-Z-but-2-ene-oate)-2-oxo-3S-phenylacetamido azetidine]disulfide was isolated as a yellow foam (247 mg, 62% yield) i.r. (CHCl$_3$) 1785 cm$^{-1}$; n.m.r. (CDCl$_3$) δ2.00 (s, 3, CH$_3$), 3.52 (s, 2, CH$_2$Ph), 4.90 (dd, J=2 and 8 Hz, 1, C$_3$—H), 5.2 (br. s, 2, CO$_2$CH$_2$Ph) 5.33 (d, J=2 Hz, 1, C$_4$—H), 7.25 (s, 10, aromatic H), 7.60 (d, J=8 Hz, 1, N—H), 9.8 (s, 1, CHO); u.v. λ$_{max}$ (CHCl$_3$)=291 nm, (ε=14,567).

Analysis: Calculated for C$_{58}$H$_{50}$N$_4$O$_{10}$S$_2$: C, 63.14; H, 4.84; N, 6.40; O, 18.28; S, 7.33; Found: C, 63.21; H, 4.97; N, 6.16; O, 18.40; S, 7.08.

PREPARATION 5

4R,4'R bis[1-(tert-butyl 2-N-3-methyl-4-al-Z-but-2-ene-oate)-2-oxo-3S-(2-isobutoxycarbonylamino-2-phenylacetamido azetidene]disulfide.

To a solution of tert-butyl 7α-(2-isobutoxycarbonylamino-2-phenylacetamido)-2α-methoxy-3-methyl-3-cephem-4-carboxylate in methylene chloride cooled to 0° C. is added N-chlorosuccinimide. This solution is stirred for 15 minutes, and then is added to a rapidly stirring suspension of mercury dichloride and cadmium carbonate in water. The resultant reaction mixture is stirred at ambient temperature for 30 minutes and is filtered through pre-washed Celite. The methylene chloride is then separated and evaporated to dryness. The product is taken up in ethyl acetate and the ethyl acetate solution is washed with water (5×) then with saturated sodium chloride solution (1×) and is subsequently dried over magnesium sulfate. Filtration and evaporation to dryness gives crude product which is chromatographed on silica gel using 1:1 ethyl acetate:hexane as the eluant.

PREPARATION 6

4R,4'R bis[1-(p-methoxybenzyl 2-N-3-methyl-4-al-Z-but-2-ene-oate)-2-oxo-3S-phenoxyacetamido azetidine]disulfide.

To a solution of 4-methoxybenzyl 7-(2-phenoxyacetamido)-2α-methoxy-3-methyl-3-cephem-4-carboxylate in methylene chloride at 0° is added N-chlorosuccinimide. The solution is stirred for 15 minutes, then is added to a rapidly stirring suspension of mercury dichloride and cadmium carbonate in water. The mixture is stirred at ambient temperature for 30 minutes, and is filtered through pre-washed Celite. The methylene chloride is then separated and evaporated to dryness. The product is taken up in ethyl acetate and the ethyl acetate solution is washed with water (5×) then with saturated sodium chloride solution (1×) and is subsequently dried over magnesium sulfate. Filtration and evaporation to dryness gives crude product which is chromatographed on silica gel using 1:1 ethyl acetate:hexane as the eluant.

PREPARATION 7 p-Methylphenyl 4R[1-(diphenylmethyl 2-N-3-methyl-4-al-Z-but-2-ene-oate)-2-oxo-3S-phenylacetamido azetidine]disulfide.

Sodium bicarbonate (95 mg, 1.1 mmol) was dissolved in 25 ml methylene chloride then cooled to −20° C. A one molar methylene chloride solution of chlorine (1.1 ml, 1.1 mmol) was pipetted into the cooled sodium bicarbonate solution followed by the dropwise addition of a methylene chloride solution of p-methylphenylmercaptan (140 mg, 1.1 mmol dissolved in 5 ml of methylene chloride). The resultant solution was stirred at −20° C. for 0.5 hour, at the end of which time diphenylmethyl 7α-benzamido-2α-methoxy-3-methyl-3-cephem-4-carboxylate (528 mg, 1 mmol) was added and the resultant solution was stirred at 0° C. for 0.5 hour, then evaporated to dryness. The resultant residue was dissolved in ethyl acetate, and this solution was washed with sodium bicarbonate solution (2×), water (1×), sodium chloride solution (1×), dried over magnesium sulfate, filtered and evaporated to dryness. The yellow foam remaining after evaporation was absorbed on to 2.5 grams of silica and chromatographed over 7 g. of silica employing first 100 ml of toluene, then 100 ml 5% ethyl acetate/toluene and finally 150 ml of 10% ethyl acetate/toluene as the eluant. The last fraction collected yielded the desired aldehyde disulfide, p-methylphenyl 4R[1-(diphenylmethyl 2-N-3-methyl-4-al-Z-but-2-ene-oate)-2-oxo-3S-phenylacetamido azetidine]disulfide (374 mg, 59% yield); i.r. (CHCl$_3$) 1780 cm$^{-1}$; n.m.r. (CDCl$_3$) δ 1.73 (s, 3, CH$_3$), 2.20 (s, 3, toluyl CH$_3$), 3.48 (s, 2, C$\underline{H}_2$Ph), 4.68 (dd, J=3 and 8 Hz, 1, C$_3$—H), 5.35 (d, J=3 Hz, 1, C$_2$—H), 6.38 (d, J=8 Hz, 1, NH), 7.00 (s, 1, C$\underline{H}$Ph$_2$), 6.8–7.6 (m, 19, aromatic protons), 9.32 (s, 1, aldlehydic proton); u.v. (CHCl$_3$) λ$_{max}$=294 nm (ε=5,500).

PREPARATION 8

Phenyl 4R[1-(diphenylmethyl 2-N-3-methyl-4-al-Z-but-2-ene-oate)-2-oxo-3S-phenylacetamido azetidine]disulfide.

Phenylmercaptan (0.105 ml, 1 mmol) was added a solution of sodium bicarbonate (84 mg, 1 mmol) suspended in methylene chloride (25 ml) at 0° C., followed by addition of 1 molar chlorine solution (1 ml, 1 mmol, methylene chlorine solution). The reaction mixture was stirred for 2 hours at the end of which time diphenylmethyl 7α-phenylacetamido-2α-methoxy-3-methyl-3-methyl-3-cephem-4-caboxylate (528 mg, 1 mmol), dissolved in 10 ml of methylene chloride, was added to the reaction mixture. The mixture was stirred for 45 minutes at 0° C. then for an additional 15 minutes after the ice bath was removed. The solution was evaporated to dryness, dissolved in ethyl acetate, added to an aqueous sodium bicarbonate solution and stirred for 15 minutes at room temperature. After separation and removal of the aqueous layer, the ethyl acetate layer was washed successively with 1 molar hydrochloric acid solution (1×), water (1×) and sodium chloride solution (1×). The solution was then evaporated to dryness, adsorbed onto 2 grams of silica gel and chromatographed over 6 grams of silica gel, eluting successively with 100 ml of toluene, 100 ml of 5% ethyl acetate/toluene, 200 ml 8% ethyl acetate/toluene, and finally with 150 ml 12% ethyl acetate/toluene. The second fraction collected yielded the desired aldehyde, phenyl 4R[1-(diphenyl-methyl-2-N-3-methyl-4-al-Z-but-2-ene-oate)-2-oxo-3S-phenylacetamido azetidine]disulfide (163 mg., 35% yield). i.r. (CHCl$_3$) 1785 cm$^{-1}$; n.m.r. (CDCl$_3$) δ 1.73 (s, 3, CH$_3$), 3.52 (s, 2, C$\underline{H}_2$Ph), 4.65 (dd, J=3 and 7 Hz, 1, C$_3$—H), 5.37 (d, J=3 Hz, 1, C$_2$—H), 6.17 (d, J=8 Hz, 1, NH), 7.02 (s, 1, C$\underline{H}$Ph$_2$), 7.20–7.50 (m, 20, aromatic protons), 9.35 (s, 1, aldlehydic proton); u.v. (CH$_3$CN) λ$_{max}$=293 nm (ε=3,900).

PREPARATION 9

7β-Phenylacetamido-7α-methoxy-3-methyl 1-oxa β-lactam diphenylmethyl ester.

7α-Phenylacetamido-3-methyl 1-oxa β-lactam diphenylmethyl ester (121 mg, 0.25 mmol) was added to a suspension of lithium methoxide in 5 ml of dry THF (made by adding 1 ml dry methanol to 5.8 mg, 0.83 mmol of lithium in THF) under positive N$_2$ pressure at −70° C. tert-Butyl hypochlorite (0.0356 ml, 0.315 mmol) was added to this solution which was then stirred for 30 minutes at −70° C., at the end of which time trimethylphosphite (0.0075 ml) and then glacial acetic acid (0.0625 ml) were added to the solution to quench the reaction. The reaction mixture was allowed to warm to ambient temperature, was evaporated to dryness, and the residue was dissolved in ethyl acetate/water solution and washed sequentially with 1 molar hydrochloric acid solution (1×), brine (1×), 5% sodium bicarbonate solution (1×), water (1×), and brine (1×). The washed solution was dried over magnesium sulfate, filtered and then evaporated to dryness to give a white foam of the product 7β-phenylacetamido-7α-methoxy-3-methyl 1-oxa β-lactam diphenylmethyl ester (123 mg). Recrystallization from acetone gave white crystals, (mp. 187°-187.5° C.) (88% yield): i.r. (CHCl$_3$) 1780 cm$^{-1}$; n.m.r. (d$_6$-acetone) δ 1.99 (s, 3, CH$_3$), 3.46 (s, 3, OCH$_3$), 3.68 (s, 2, C$\underline{H}_2$Ph), 4.34 (br. s, 2, C$_2$—H), 5.05 (s, 1, C$_6$—H), 6.91 (s, 1, C$\underline{H}$Ph$_2$), and 7.3 (m, 16, aromatic H and N—H); mass spectrum, m/e 512.

PREPARATION 10

7β-Phenylacetamido-7α-methoxy-3-methyl 1-oxa β-lactam acid.

7β-Phenylacetamido-7α-methoxy-3-methyl 1-oxa β-lactam diphenylmethyl ester (50 mg. 0.01 mmol) was dissolved in 0.1 ml of anisole, cooled to 0° C., and trifluoroacetic acid (0.4 ml) was slowly added to the reaction mixture. The reaction mixture was stirred for 10 minutes at 0° C., was diluted with ethyl acetate, was evaporated at ambient temperature, and the resulting colorless oil was taken up in 20 ml of ethyl acetate at 0° C. Cold water (10 ml) was added to the ethyl acetate solution, the resulting slurry was adjusted to pH 8 with 0.04 molar sodium hydroxide solution and the layers were then separated. Ten ml of ethyl acetate at 0° C. was added to the water layer, and the pH of the resulting slurry was adjusted to pH 3.0 (at 0° C.) with 0.04 molar hydrochloric acid. The layers were separated, and the ethyl acetate layer was washed with saturated sodium chloride solution (1×), dried over magnesium sulfate, filtered and evaporated to dryness. The crude product was recrystallized from acetone to give pure 7β-phenylacetamido-7α-methoxy-3-methyl 1-oxa β-lactam acid (20 mg, 59% yield) (mp 169°-170° C.): i.r. (KBr) 1782 cm$^{-1}$; n.m.r. (d$_6$-acetone) δ 2.00 (s, 3, CH$_3$), 3.43 (s, 3, OCH$_3$), 3.53 (s, 2, C$\underline{H}_2$Ph), 4.39 (br. s, 2, C$_2$—H), 5.07 (s, 1, C$_6$—H), 5.70 (br. s, 1, COOH), 7.33 (s, 5, aromatic H), and 7.95 (s, 1, N—H).

We claim:

1. The process for preparing a 7α-acylamino-3-methyl 1-oxa β-lactam compound of the formula

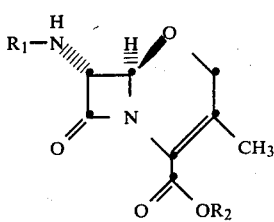

which comprises reacting a compound of the formula

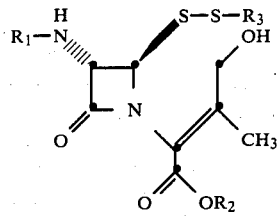

with a cyclization reagent selected from the group consisting of
(a) a divalent mercury compound of the formula $Hg(X)_2$ wherein X is chloro, bromo or trifluoroacetato; and
(b) a phosphine compound of the formula $(R_5)_3P$ wherein each $R_5$ is independently $C_1$ to $C_7$ alkyl, phenyl or phenyl substituted with $C_1$ to $C_4$ alkyl or $C_1$ to $C_4$ alkoxy, in an inert organic solvent with between about 1 to about 5 moles of said cyclizing reagent per mole of said azetidinone alcohol disulfide compound;

wherein the above formulae $R_1$ is an acyl group of the formula

wherein R' is
(a) $C_1$–$C_7$ alkyl, cyanomethyl, $C_1$–$C_6$ haloalkyl, 4-protected amino-4-protected carboxybutyl; or
(b) $C_1$–$C_6$ alkoxy, phenoxy, benzyloxy or 4-methoxybenzyloxy; or
(c) the group —R″ wherein R″ is phenyl, or substituted phenyl wherein the substituents are 1 or 2 halogens, protected hydroxy, cyano, trifluoromethyl, $C_1$–$C_4$ alkyl, $C_1$–$C_4$ alkoxy, protected carboxy, protected carboxymethyl, protected hydroxymethyl or protected aminomethyl; or
(d) an arylalkyl group of the formula

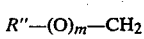

wherein m is 0 or 1; or
(e) a substituted arylalkyl group of the formula

wherein R‴ is R″ as defined above, 2-thienyl, 3-thienyl, 2-furyl or 3-furyl; W is protected hydroxy, protected carboxy, protected amino, or
(f) a heteroarylmethyl group of the formula

R″″—CH₂— wherein R″″ is 2-thienyl, 3-thienyl, 2-furyl, 3-furyl, 2-thiazolyl, 5-tetrazolyl, 1-tetrazolyl;

$R_2$ is a carboxy protecting group and $R_3$ is another identically substituted substituted azetidinone alcohol moiety bonded to the opposite end of the disulfide group, or is phenyl or a mono-substituted phenyl, where the substituents are chloro, methoxy, methyl or acetoxy.

2. The process of claim 1 wherein $R_2$ is diphenylmethyl, tert-butyl, p-methoxybenzyl, 2,4,6-trimethylbenzyl, trityl, 4-methoxytrityl, 4,4'-dimethoxytrityl, 4,4',4″-trimethoxytrityl.

3. The process of claim 1 wherein $R_3$ is phenyl or p-methylphenyl.

4. The process of claim 1 wherein $R_3$ is phenyl or mono-substituted phenyl, where the substituents are chloro, methoxy, methyl or acetoxy.

5. The process of claim 4 wherein $R_2$ equals is an acyl group of the formula

wherein R' is
(a) $C_1$–$C_7$ alkyl, cyanomethyl;
(b) $C_1$–$C_6$ alkoxy;
(c) benzyl, 1-phenoxymethyl, 1-p-methoxyphenylmethyl;
(d) 2-thienylmethyl, 3-thienylmethyl 2-furylmethyl, 3-furylmethyl, 2-thiazolylmethyl, 5-tertazolylmethyl;
(e) 1-protected hydroxy-1-phenyl-methyl, 1-protected amino-1-phenylmethyl, 1-protected amino-1-(4-protected hydroxyphenyl)methyl.

6. The process of claim 5 wherein $R_2$ is diphenylmethyl, tert-butyl, p-methoxybenzyl, 2,4,6-trimethylbenzyl, trityl, 4-methoxytrityl, 4,4'-dimethoxytrityl and 4,4',4″-trimethoxytrityl.

7. The process of claim 6 wherein $R_2$ is diphenylmethyl.

8. The process of claim 1 wherein $R_3$ is phenyl or a mono-substituted phenyl, where the substituents are chloro, methoxy, methyl or acetoxy.

9. The process of claim 8 wherein $R_2$ equals an acyl group of the formula

wherein R' is
(a) $C_1$–$C_7$ alkyl or cyanomethyl;
(b) $C_1$–$C_6$ alkoxy;
(c) benzyl, 1-phenoxymethyl, 1-p-methoxyphenylmethyl;
(d) 2-thienylmethyl, 3-thienylmethyl, 2-furylmethyl, 3-furylmethyl, 2-thiazolylmethyl, 5-tetrazolylmethyl;
(e) 1-protected hydroxy-1-phenylmethyl, 1-protected amino-1-phenylmethyl, 1-protected amino-1-(4-protected hydroxyphenyl)methyl.

10. The process of claim 9 where $R_3$ is phenyl or p-methylphenyl.

11. The process of claim 10 wherein $R_2$ is diphenylmethyl, tert-butyl, p-methoxybenzyl, 2,4,6-trimethylbenzyl, trityl, 4-methoxytrityl, 4,4'-dimethoxytrityl and 4,4',4''-trimethoxytrityl.

12. The process of claim 11 wherein $R_2$ is diphenylmethyl.

13. The process of claim 1 wherein $R_3$ is another molecule of the identically substituted azetidinone alcohol moiety bonded to the opposite end of the disulfide group.

14. The process of claim 13 wherein $R_1$ is an arylalkyl group of the formula

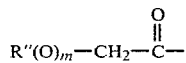

wherein R'' is phenyl or substituted phenyl wherein the substituents are 1 or 2 halogens, protected hydroxy, cyano, trifluoromethyl, $C_1$–$C_4$ alkyl, $C_1$–$C_4$ alkoxy, protected carboxy, protected carboxymethyl, protected hydroxymethyl or protected aminomethyl; and m is 0 or 1.

15. The process of claim 14 wherein $R_2$ is diphenylmethyl, tert-butyl, p-methoxybenzyl, 2,4,6-trimethylbenzyl, trityl, 4-methoxytrityl, 4,4'-dimethoxytrityl, 4,4',4''-trimethoxytrityl.

16. The process of claim 15 wherein $R_1$ is benzoyl.

17. The process of claim 16 wherein $R_2$ is diphenylmethyl.

18. The process of claim 1 wherein $R_3$ is phenyl or a mono-substituted phenyl, where the substituents are chloro, methoxy, methyl or acetoxy.

19. The process of claim 18 wherein $R_1$ is an arylalkyl group of the formula

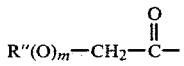

wherein R'' is phenyl or substituted phenyl wherein the substituents are 1 or 2 halogens, protected hydroxy, cyano, trifluoromethyl, $C_1$–$C_4$ alkyl, $C_1$–$C_4$ alkoxy, protected carboxy, protected carboxymethyl, protected hydroxymethyl or protected aminomethyl; and m is 0 or 1.

20. The process of claim 19 wherein $R_3$ is phenyl or p-methylphenyl.

21. The process of claim 20 wherein $R_2$ is diphenylmethyl, tert-butyl, p-methoxybenzyl, 2,4,6-trimethylbenzyl, trityl, 4-methoxytrityl, 4,4'-dimethoxytrityl, 4,4',4''-trimethoxytrityl.

22. The process of claim 21 wherein $R_1$ is benzoyl.

23. The process of claim 22 wherein $R_2$ is diphenylmethyl.

24. The process of claim 23 wherein $R_3$ is phenyl.

25. The process of claim 23 wherein $R_3$ is p-methylphenyl.

26. The process of claims 1, 5, 9, 14, 17, 19, 24 or 25 wherein the cyclization agent is either bis(trifluoroacetato)mercury(II) or triphenylphosphine.

* * * * *